United States Patent [19]
Nash et al.

[11] Patent Number: 5,625,455
[45] Date of Patent: Apr. 29, 1997

[54] ROTATING ANALYZER ELLIPSOMETER AND ELLIPSOMETRY TECHNIQUE

[75] Inventors: Patrick L. Nash; Robert J. Bell, both of San Antonio, Tex.

[73] Assignee: Board of Regents, The University of Texas System, Austin, Tex.

[21] Appl. No.: 466,041

[22] Filed: Jun. 6, 1995

[51] Int. Cl.$^6$ .................................................. G01N 21/21
[52] U.S. Cl. ........................................................ 356/369
[58] Field of Search ........................... 356/364, 365, 356/366, 367, 368, 369

[56] References Cited

U.S. PATENT DOCUMENTS

| | | | |
|---|---|---|---|
| 3,880,524 | 4/1975 | Dill et al. | 356/369 |
| 4,077,720 | 3/1978 | Kasai | 356/118 |
| 4,097,110 | 6/1978 | Carey | 350/149 |
| 4,176,951 | 12/1979 | Robert et al. | 356/33 |
| 4,585,348 | 4/1986 | Chastang et al. | 356/369 |
| 4,672,196 | 6/1987 | Canino | 250/225 |
| 4,725,145 | 2/1988 | Azzam | 356/367 |
| 4,906,844 | 3/1990 | Hall | 250/225 |
| 4,941,138 | 7/1990 | Chida et al. | 369/44.41 |
| 4,967,152 | 10/1990 | Patterson | 324/158 R |
| 5,042,951 | 8/1991 | Gold et al. | 356/369 |
| 5,076,696 | 12/1991 | Cohn et al. | 356/369 |
| 5,181,080 | 1/1993 | Fanton et al. | 356/381 |
| 5,247,176 | 9/1993 | Goldstein | 356/367 |
| 5,329,357 | 7/1994 | Berroux et al. | 356/369 |

OTHER PUBLICATIONS

Aspnes and Studna, "High Precision Scanning Ellipsometer," *Applied Optics*, 14(1):220–228, 1975.

Ianno et al., "Is situ Spectroscopic Ellipsometry Studies of Electron Cyclotron Resonance (ECR) Plasma Etching of Oxides of Silicon and GaAs," *Elsevier Science Publishers*, 19–21, 1993.

Yao and Woollam, "Spectroscopic Ellipsometric Characterization of Si/Si$_{1-x}$Ge$_x$Strained–Layer Superlattices," *Elsevier Science Publishers*, 52–56, 1993.

Yakovlov et al., "Infrared Rotating–Analyzer Ellipsometry: Calibration and Data Processing," *Optical Society of America* 10(3):509–514, 1993.

*Primary Examiner*—Richard A. Rosenberger
*Attorney, Agent, or Firm*—Arnold, White & Durkee

[57] ABSTRACT

A novel ellipsometer and ellipsometry technique are disclosed that allow the determination of optical and spectroscopic properties of a sample material. In particular, the complex dielectric constant ($\epsilon$) and the complex index of refraction (N) of a sample material are determined from simple reflectance intensity measurements at a single frequency. The disclosed invention may be used to determine desired optical and spectroscopic properties of a variety of sample materials, including solid and fluid materials. The disclosed method and apparatus for determining these properties are not dependent upon numerical approximations or frequency scans. The disclosed invention has a broadband working frequency range and may take advantage of radiation sources providing elliptically-polarized incident radiation, such as new solid-state lasers. The disclosed invention thereby provides a significant advance over prior ellipsometer devices and ellipsometry techniques.

15 Claims, 6 Drawing Sheets

ROTATING ANALYZER ELLIPSOMETER AND ELLIPSOMETRY TECHNIQUE

BACKGROUND OF THE INVENTION

1. Field of Invention

This invention relates to ellipsometry. More particularly, it relates to a novel ellipsometer and ellipsometry analysis technique that allow the dielectric constant and the complex index of refraction for a sample material to be determined without the need for wavelength dependent numerical approximations and frequency scans.

2. Background

Ellipsometry techniques are based upon the fact that a linearly-polarized light vibration may be resolved into two perpendicular vibrations that are in phase. One of these vibrations is in the incidence plane and the other is in a plane normal to the incidence plane. After reflection or transmission, these vibrations undergo amplitude and phase changes which are generally different. Thus, the light is then elliptically-polarized. An ellipsometer generally measures the changes in the state of polarization and includes a monochromatic light source, collimators, a polarizer with or without a quarter wavelength plate, a surface, an analyzer and a photo detector.

The polarization of the light reflecting off a sample is measured and analyzed to determine the variations in that polarization from the incident light. For this analysis, existing techniques generally have used a polarizer, a quarter wavelength plate, and an analyzer. The polarizer and the analyzer are rotated to obtain the respective angles for the polarizer and the analyzer at which the reflected light from the sample is extinguished by the analyzer. From these angles, the variables of polarized light can be calculated, such as the phase difference (delta) and the amplitude-reflection ratio angle (psi).

Prior ellipsometry techniques are often used to determine the thickness of thin films on solid materials, such as an oxide layer thickness on a semiconductor material. Prior ellipsometry techniques, devices and analyses, however, require the use of numerical approximations to determine certain properties of the sample material, such as the dielectric constant and complex index of refraction. Further, prior ellipsometry techniques, devices and analyses do not provide for the quick, direct, and accurate analysis of spectroscopic properties of sample materials, including properties of biological fluids, such as the saline content in a blood sample.

The object of the present invention is to provide a novel ellipsometer device and ellipsometry technique that allows the direct determination of optical and spectroscopic properties of sample materials, such as the complex dielectric constant and complex index of refraction.

SUMMARY OF THE INVENTION

The present invention contemplates a novel ellipsometer and ellipsometry technique that determine the complex dielectric constant ($\epsilon$) of a sample material at a single frequency from simple reflectance intensity measurements at that frequency. The present invention may be used to determine desired spectroscopic properties of a wide variety of sample materials, including solid and fluid materials. By providing a method and apparatus for determining these properties without the need for numerical approximations or frequency scans, the present invention provides a significant advance over prior ellipsometer devices and ellipsometry techniques.

An ellipsometer device according to the present invention can operate over a wide range of optical wavelengths from the infrared (approximately 7000 nm) to the ultraviolet ("UV") (200 nm) spectral range. This coverage range is unprecedented. In particular, an ellipsometer according to the present invention may be constructed to function in the visible spectral range (e.g., 632.8 nm). The novel spectrometer/ellipsometer system of the present invention may also take advantage of tunable laser systems, such as the new tuneable lasers (UV to 7,000 nm) that utilize frequency doubling materials. To irradiate a sample, therefore, the present invention may employ a wide range of radiation sources that can provide elliptically-polarized monochromatic electromagnetic-radiation. Preferably, this incident radiation will be circularly-polarized.

The ellipsometry technique of the present invention allows the determination of complex optical parameters and spectroscopic properties of a sample material without approximations. The technique of the present invention analyzes the radiation reflected or transmitted by the sample material to determine modifications to the incident radiation due to interactions with the sample material. According to the unique analysis of the present invention, the complex index of refraction, the complex dielectric constant, the transmittance, the reflectance, the absorption coefficient, the optical density, and other optical properties of the sample material may be obtained without the need for numerical approximations.

The novel ellipsometry technique of the present invention allows sample materials to be studied with incident radiation at any angle of incidence between zero and ninety degrees. This angle of incidence may be chosen depending upon the size of the sample material that is available. Thus, the ellipsometer system of the present invention requires only arbitrary, elliptically-polarized incident radiation at any convenient angle of incidence. In contrast, prior ellipsometry techniques required circularly-polarized radiation falling on the sample and an angle of incidence equal to the principal angle (which can be very large) for the sample material.

Utilizing the novel ellipsometry technique of the present invention, the digitized intensity data obtained from the radiation reflected or transmitted by the sample material is analyzed using integrals (or sums). These integrals cancel signal noise in determining optical parameters and allows the frequency scan to be commenced and terminated at any common, arbitrary, angular position of the analyzing polarizer. In contrast, prior ellipsometry techniques have required analysis at the principle angle for the sample material, which can require an angle of incidence as high as seventy to eighty degrees.

One embodiment of an ellipsometry method for determining optical and spectroscopic properties of a material according to the present invention, includes: subjecting a material to an incident radiation having a determined elliptical polarization state; measuring a resultant radiation from the material due to interaction with the incident radiation; creating digitized intensity data for the resultant radiation; and utilizing the digitized intensity data to determine a complex index of refraction or a complex dielectric constant for the material. In so doing, the method also includes: analyzing the digitized intensity data (I) to obtain values for U and $\beta$ utilizing the equation:

$$I = I_{ave}[1 + U\sin(2\psi + \beta)],$$

the values for U and $\beta$ representing the polarization state of the resultant radiation; utilizing an angle of incidence ($\theta$) for the incident radiation; utilizing a principle angle ($\theta^p$) for the material; calculating a value for the complex Fresnel coefficient (F) utilizing the equation F =x+iy, where $$y = \cos(\beta)U \frac{1+\cos^2(2\theta) - \sin(\beta)\sin^2(2\theta)U + (\eta)2\cos(2\theta)\sqrt{1-U^2}}{\sin^2(2\theta) - 2U\sin(\beta)[1+\cos^2(2\theta)] + U^2 \left[ \frac{(1+\cos^2(2\theta))^2}{\sin^2(2\theta)} - \cos^2(\beta)\sin^2(2\theta) \right]} \qquad (1.3)$$

the value for $\eta$ being $-1$ for $0<\theta<\theta^p$, and the value for $\eta$ being $+1$ for $\theta^p<\theta<\pi/2$, and $$x = -\sqrt{1 + 2y\tan(\beta) - y^2} \ ; \qquad (1.4)$$

and calculating a value for the dielectric constant ($\epsilon$) utilizing the equation:

$$\epsilon = \frac{1 - 2F\cos(2\theta) + F^2}{(1+F)^2} \qquad (1.2)$$

Another embodiment of an ellipsometry method for determining optical and spectroscopic properties of a material according to the present invention, includes: subjecting a material to incident radiation having a determined elliptical polarization state; measuring a resultant radiation from the material due to interaction with the incident radiation; determining a polarization state for the resultant radiation; and utilizing digitized intensity data at a single frequency to determine an optical property of the material from modifications to the known polarization state of the incident radiation due to interaction with the material. For this ellipsometry method, the resultant radiation may be radiation reflected by the material due to interaction with the incident radiation and/or radiation transmitted through the material due to interaction with said incident radiation. This ellipsometry method may be used to determine properties of a variety of materials, including solid, homogenous material and fluid biological material.

A further embodiment of the present invention is a rotating-analyzer ellipsometer for determining optical and spectroscopic properties of a material. This apparatus includes: a radiation source providing incident radiation of a definite polarization and frequency directed toward a material at a measureable angle of incidence; a polarization insensitive radiation detector positioned to receive resultant radiation after interaction of the incident radiation with the material; and a computer-controlled data analysis means for utilizing digitized intensity data for the resultant radiation to determine modifications to the polarization state of the incident radiation due to interaction with the material and to determine optical and spectroscopic properties of the material as a function of the modifications to the polarization state.

As a further embodiment, the rotating-analyzer ellipsometer can have a computer-controlled data analysis means that utilizes digitized intensity data at a single frequency. The radiation source may include: a solid state laser; a linear polarizer in optical communication with the solid state laser; and a Fresnel Rhomb in optical communication with the linear polarizer. The detector may include: a rotating linear polarizer (analyzer); an integrating sphere in optical communication with the rotating linear polarizer; and a photo detector in optical communication with the integrating sphere. Further, the ellipsometer can determine the complex index of refraction and the complex dielectric constant for the material.

The advantages of the present invention will be further appreciated from the drawings and from the detailed description provided below.

BRIEF DESCRIPTION OF THE DRAWINGS

The herein described advantages and features of the present invention, as well as others which will become apparent, are attained and can be understood in more detail by reference to the following description and appended drawings, which form a part of this specification.

It is to be noted, however, that the appended drawings illustrate only exemplary embodiments of the invention and are therefore not to be considered limiting of its scope, for the invention may admit to other equally effective embodiments.

DETAILED DESCRIPTION

The present invention provides a novel ellipsometer and ellipsometry technique for analyzing optical data and determining optical and spectroscopic properties of a sample material. The present invention allows a researcher to obtain the optical constants of a sample at a single frequency from measurements at that frequency. No frequency scan is necessary. Moreover, no physical models are invoked at low or high frequencies, as must be done in the Kramer-Kronig analysis. These physical models have been necessary using prior ellipsometry techniques to extend the integration: (1) down to zero from the lowest frequency for which a reflectance is recorded and (2) up to infinity from the highest frequency for which a reflectance is measured. In further contrast to prior ellipsometry techniques and formulations, the present invention requires no numerical approximations and utilizes straightforward, accurate and robust numerical algorithms for analysis of optical data.

1. Ellipsometer System

Figure 1:
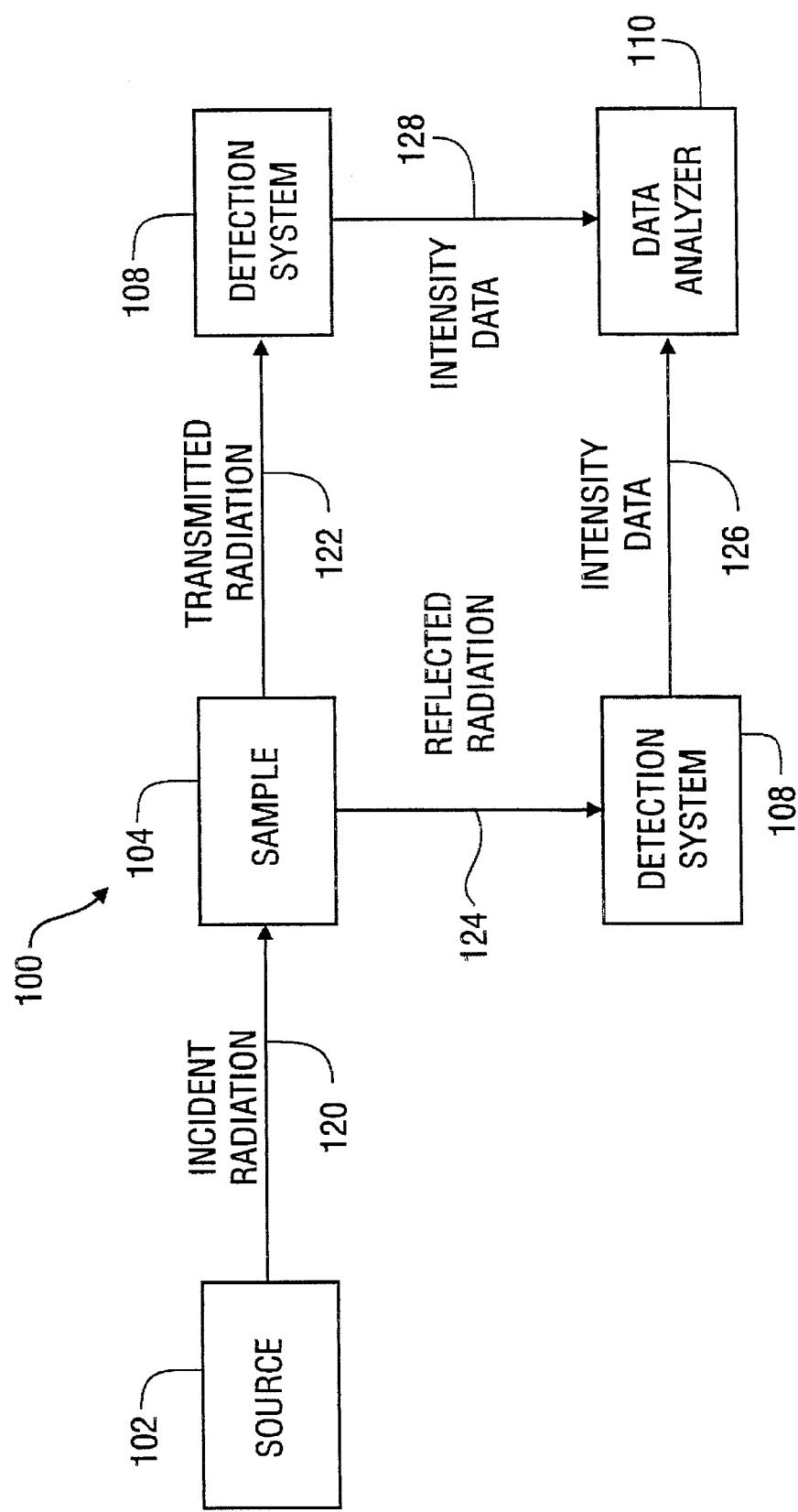
FIG. 1 is a block diagram of an ellipsometer according to the present invention.

FIG. 1 is a block diagram of one embodiment of an ellipsometer according to the present invention. Ellipsometer 100 includes a radiation source 102, a sample material 104, detection systems 108, and a data analyzer 110. Radiation source 102 provides incident radiation 120 having a definite frequency and a definite polarization state. The frequency and polarization state of incident radiation 120 may be determined utilizing detection system 108 prior to making measurements with the sample material 104 in place.

Incident radiation 120 strikes sample material 104 and may be reflected, transmitted or both by sample material 104. Detection systems 108 may be used to detect the reflected radiation 124 and/or the transmitted radiation 122. Detection system 108 provides optical intensity data, including the resulting frequency and polarization states, of the reflected or transmitted radiation to the data analyzer 110.

Figure 2:
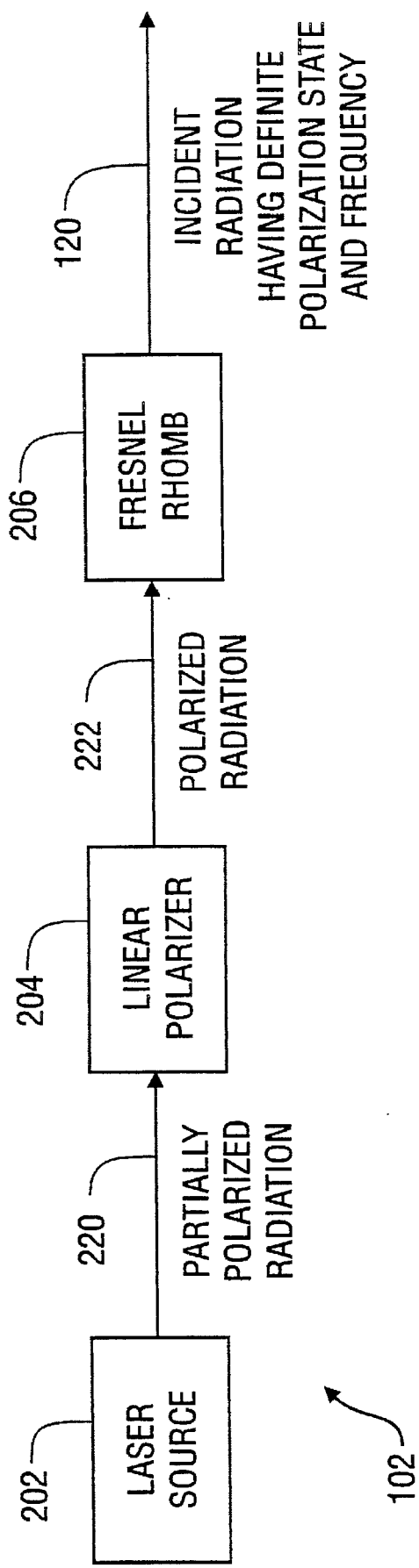
FIG. 2 is block diagram of a radiation source for an ellipsometer according to the present invention.

FIG. 2 is a block diagram of an embodiment of a radiation source 102 for an ellipsometer according to the present invention. Source 102 may include a laser source 202, a linear polarizer 204, and a Fresnel rhomb 206. Laser source 202 provides radiation that is generally, partially polarized. Partially polarized radiation 220 is transmitted through a linear polarizer 204 to provide polarized radiation 222. Fresnel rhomb 206 adds a definite frequency to polarized radiation 222. Thus, radiation source 102 provides incident radiation 120 having a definite frequency and polarization state.

For the laser source, the present invention may take advantage of new room-temperature tuneable, coherent lasers and other solid state devices. By using these devices, the present invention provides an ideal, successful, commercial instrument that may utilize a strong, stable, coherent and broadband radiation source. For example, the present invention may use 400 to 2,000 nm wavelength range tuneable lasers (OPO type) that are available from Spectra-Physics Lasers, Inc. Although one may preferably use a laser providing radiation well into the infrared range, such a laser will often require the further complication of atmosphere purging. Atmospheric windows may also be used if needed.

For the linear polarizer and Fresnel Rhomb, the present invention may use a broad range of available devices. For example, in the visible/infrared ranges, incident radiation of a definite frequency and polarization state may be created using a Glan-laser polarizer followed by Babinet-Soleil compensator or Fresnel rhomb. A $MgF_2$ Rochon prism polarizer and a $CaF_2$ Fresnel rhomb may also be used for most of the infrared range. Linear polarizers based on parallel wire properties may also be used in the present invention.

To forestall problems with optical component mounting and vibrations, an isolation table may be used. Further, to facilitate the initial alignment of the optical components in the system, a plurality of 5-axis optical mounts and a large goniometer may be used.

Figure 4:
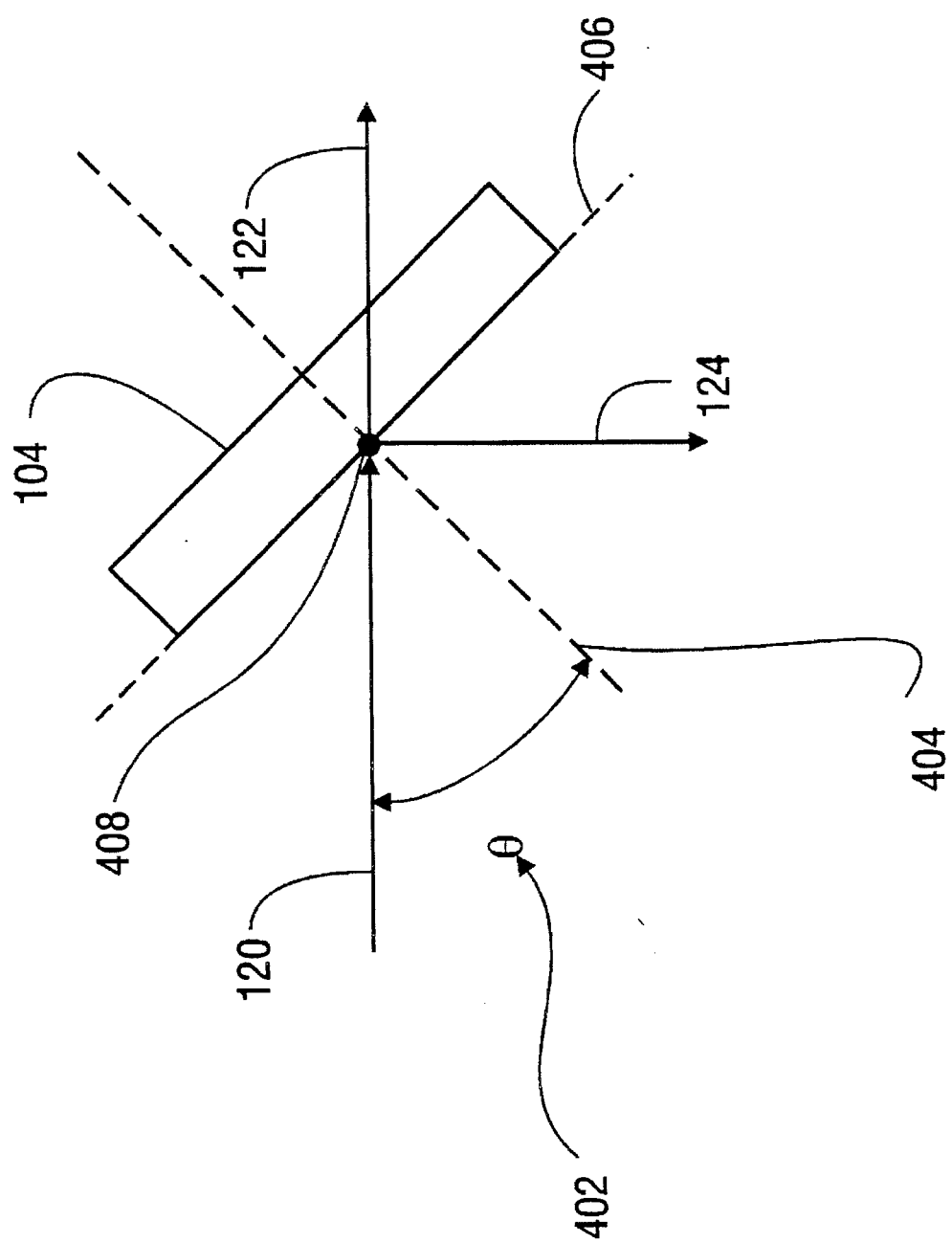
FIG. 4 is a diagram of the orientation of the sample material with respect to the incident, reflected and transmitted radiation according to the present invention.

FIG. 4 is a diagram of an orientation of the sample material for the ellipsometer according to the present invention. Sample material 104 is positioned at an angle to incident radiation 120. Line 406 represents the plane of sample material 104, and line 404 represents a perpendicular plane to sample material 104. Line 404 and line 406 are therefore perpendicular.

Point 408 represents the point at which incident radiation 120 strikes sample material 104. Angle 402 represents the angle of incidence (θ) between incident radiation 120 and the perpendicular line 404. Angle 402 may be between 0 and 90 degrees for the present invention. After striking sample material 104, incident radiation 120 is reflected by the sample material 104 into reflected radiation 124 and/or transmitted through the sample material 104 into transmitted radiation 122.

The present invention may be used to determine optical and spectroscopic properties of a wide variety of materials, including fluid materials, as sample material 104. For example, the sample material may be optically dense solid materials, such as metals, graphite, heavily doped semiconductors, conducting polymers, sample charged pressed pellets, etc. The sample material may also be a fluid material, such as blood and other biological fluids. Further, because the present invention can work at angles of incidence far less than the principle angle of the sample material, smaller sample material sizes may be studied with the present invention.

Figure 3:
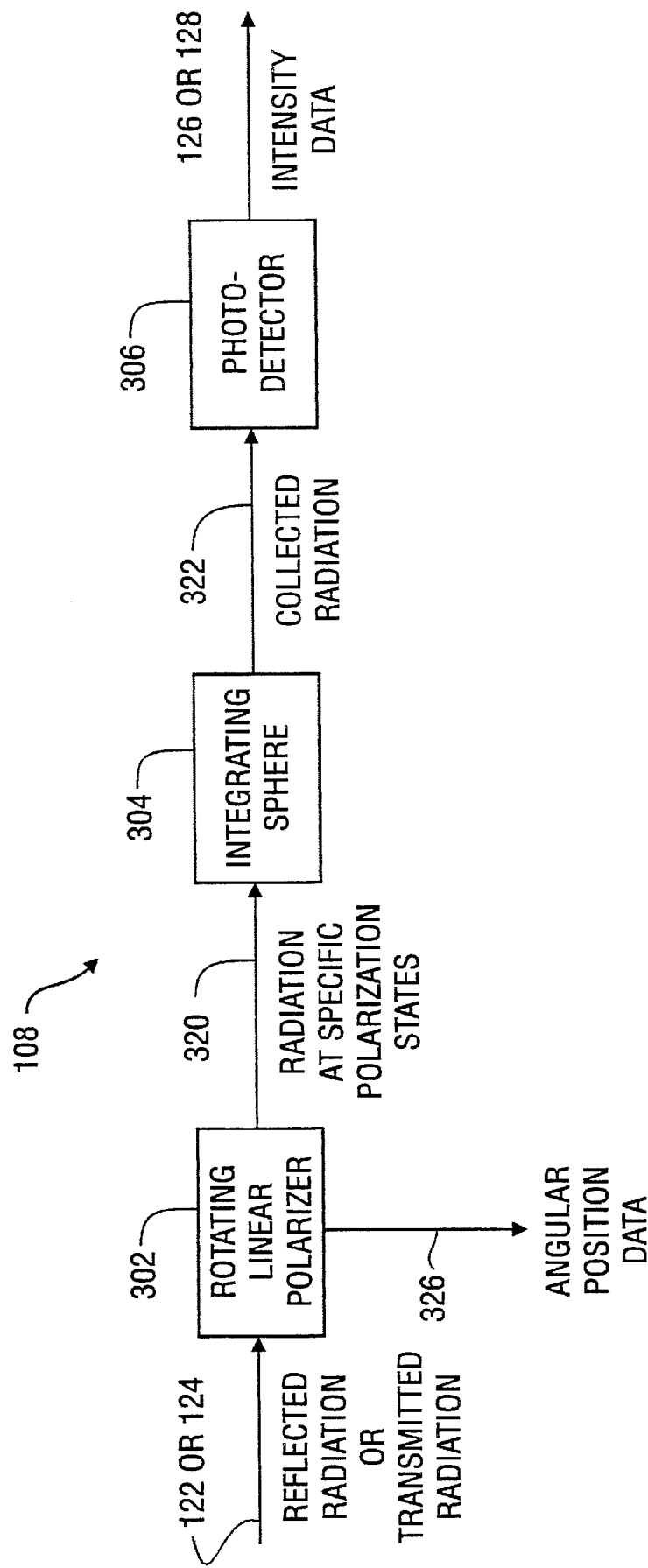
FIG. 3 is a block diagram of a detection system for an ellipsometer according to the present invention.

FIG. 3 is a block diagram of one embodiment of a detection system for an ellipsometer according to the present invention. Detection system 108 may include a rotating linear polarizer (analyzer) 302, an integrating sphere 304, and a photo detector 306. The analyzer 302 is aligned with reflected radiation 124, or transmitted radiation 122, such that it through analyzer 302. The radiation 320 that passes through analyzer 302 has specific polarization states depending upon the position of analyzer 302 as it rotates. Data regarding the angular position 326 of the analyzer 302 is sent to data analyzer 110.

Radiation 320 is then focused into an integrating sphere 304. Integrating sphere 304 collects radiation 320 as represented by collected radiation 322. A photo detector 306 is mounted on integrating sphere 304 and detects collected radiation 322 through a port in the integrating sphere 304. Thus, collected radiation 322 leaves the port in the integrating sphere 304 and strikes photo detector 306. Photodetector 306 thereby measures the intensity of the radiation entering the integrating sphere 304 as a function of the rotation angle of the analyzer 302. Data from photodetector 306 concerning intensity of radiation is digitized (with an analog-to-digital (A/D) converter) and sent to data analyzer 110. This digitized data represents intensity data 126 for reflected radiation 124 or intensity data 128 for transmitted radiation 122.

The detection system may consist of a synchronous motor driving the analyzing polarizer, a control disk to designate each angular position of the analyzer, a mirror/lens/detector system to designate every full rotation of the analyzer, a lens to focus the radiation from the sample/analyzer into an integrating sphere, an integrating sphere that scrambles the state of polarization coming from the sample, an interior baffle to keep any direct radiation from reaching the photo detector, and the photo detector mounted at a small, side port of the integrating sphere. The entire system may be provided with an overall, black interior radiation shield.

The rotating linear polarizer (analyzer) 302 for the visible/IR range may be a Glan-laser linear polarization analyzer mounted on a precision rotary table having 0.01 degrees accuracy and 0.001 degree resolution. The analyzer is generally computer controlled. The drive system for the analyzer may be continuously rotated using the rapid scan/electronic mode, which is commonly used with Fourier Transform Spectroscopy ("FTS"). This mode can be used to evaluate the DC ($I_{ave}$) and AC ($I_{ave}*U$) components of the radiation intensity (I), even though this information is not necessary for the ellipsometry technique of the present invention. Computer fitting of the data is also an option to obtain I(t) curves.

An integrating sphere 304 (with a source shielding baffle) is used because detection system 108 should be insensitive to radiation polarization. The photo detector 306 may then be located at a side port of integrating sphere 304 such that no direct radiation reaches it.

To evaluate all of the radiation frequency ranges, a wide-band detector system is used because of the relatively wide, broadband nature of the ellipsometer according to the present invention. Further, radiation filtering, electronic circuits, rhombs, parallel wire grids, radiation filters, collimators, etc., may be modified within the ellipsometer of the present invention to achieve the results desired.

The detector output voltage and analyzer angular position are sent to a data analyzer 110. Data analyzer 110 may be a computer, e.g., Intel 486 microprocessor (16Mhz) machine, implementing the analysis technique according to the present invention. This software controlled computer analysis determines optical constants for the sample material 104, namely the complex index of refraction N, the real index of refraction (n), the extinction coefficient (k), and the dielectric constant ($\epsilon$). These optical properties have the following relationship: $\epsilon=N^2=(n+ik)^2$. Other optical properties of the sample material 104 may also be determined, including but not limited to the reflectance/reflectivity, the transmittance/transmissivity, or the absorption coefficients. These optical properties, once determined, may be output on a computer disk, a paper printout, or an appropriate plot at any wavelength.

In operation, the sample material 104 modifies the polarization state of incident radiation 120. By analyzing the changes in the polarization state, an ellipsometer utilizing the novel ellipsometry technique according to the present invention allows the determination of optical properties, such as the dielectric constant and the complex index of refraction, without the need for numerical approximations. The detection system 108 measures the intensity of the reflected radiation 126 and/or transmitted radiation 128 through 180° of rotation of the analyzer 302. Although circularly-polarized incident radiation simplifies the calculations for determining the optical properties, elliptically-polarized radiation may be used according to the present invention.

In addition to analyzing the transmitted or reflected radiation as a function of analyzer rotational position in time, the same determinations may be made at several angles of incidence using care to avoid near normal incidence and taking care to note the principal angle. The principle angle, or polarizing angle, is the angle of incidence for p-type polarization at which the reflectance is a minimum.

The novel ellipsometry technique and ellipsometer according to the present invention determines the optical properties of a sample from reflectance or transmittance measurements at a single frequency.

2. Ellipsometry Technique

An outline of the novel ellipsometer and ellipsometry technique according to the present invention is now given.

This discussion is followed by a description of an embodiment of the computer software implementation used to find the dielectric parameters of the sample (real and imaginary parts) from the digitized intensity data.

The complex dielectric constant $\epsilon$ of a sample material is determined from reflectance measurements at a single frequency using an ellipsometer according to the present invention. Radiation source 102 preferably provides monochromatic, circularly-polarized (helicity eigenstate) radiation incident on an isotropic, homogeneous sample at angle of incidence $\theta$ as shown in FIG. 4. This radiation is reflected from sample material 104 through rotating linear polarizer 302 located in front of the polarization insensitive radiation detector (e.g., integrating sphere 304 and photodetector 306). The signal intensity detected is recorded as a function of the relative polarizer/analyzer orientation. From these measurements, $\epsilon$ is determined. Approximate solutions to experimental setups that do not employ circularly-polarized radiation are well known, such as those described by R. M. A. Azzam and N. M. Bashara in *Ellipsometry and Polarized Light* (North Holland, N.Y., 1992); p. 257, 414.

In contrast to these prior ellipsometry techniques, the present invention provides an exact determination technique, with an emphasis on elliptically-polarized radiation sources. The technique of the present invention does not resort to any wavelength dependent numerical approximations, which characterize many ellipsometry techniques, and does not use the Kramers-Kronig formalism and the frequency scans demanded by the Kramers-Kronig analysis.

For elliptically-polarized radiation incident on the sample the signal at the detector may be represented by the following equation:

$$I=I_{ave}[1+U \sin(2\psi+\beta)] \quad (1.1)$$

where $\psi$ is the angular difference between the rotation angle of the analyzer and the fixed angle of incidence $\theta$ of the incident radiation on the sample material. That is, there is a known fixed reference direction for the incident (polarizer) and the reflected (analyzer) directions. Thus, one knows exactly where the fixed axis is for both the background scan and the sample scan. This importantly means that the ellipsometer of the present invention can work with arbitrary elliptically-polarized incident radiation and is not limited to circularly-polarized incident radiation.

This data gives us $I_{ave}$, $I_{ave}U$ and $\beta$ for each sample. The relative complex dielectric constant $\epsilon$ is given by the complex Fresnel coefficient F and angle of incidence $\theta$ according to the following equation:

$$\epsilon = \frac{1 - 2F\cos(2\theta) + F^2}{(1+F)^2} \quad (1.2)$$

Putting the complex Fresnel coefficient in terms of F=x+iy, it is shown below that $$y = \cos(\beta)U \frac{1+\cos^2(2\theta) - \sin(\beta)\sin^2(2\theta)U + (\eta)2\cos(2\theta)\sqrt{1-U^2}}{\sin^2(2\theta) - 2U\sin(\beta)[1+\cos^2(2\theta)] + U^2 \left[ \frac{(1+\cos^2(2\theta))^2}{\sin^2(2\theta)} - \cos^2(\beta)\sin^2(2\theta) \right]} \quad (1.3)$$

and $$x = -\sqrt{1 + 2y\tan(\beta) - y^2} \quad (1.4)$$

These and all other mathematical results have been checked for correctness using Maple V, which is a sophisticated software package for doing symbolic mathematics. Maple V is available from Maple V, Waterloo Maple Software, 450 Phillip Street, Waterloo, Ontario, Canada N2L 5J2.

In Equation (1.3) above, $\eta=+1$ for $0<\theta<\theta^p$, and $\eta=-1$ for $\theta^p<\theta<\pi/2$. $\theta^p$ is the principal angle (polarizing angle) for the sample, defined as that angle of incidence at which the phase shifts experienced upon reflection by the p and s polarizations differ by $\pi/2$. $U(\theta)$ possesses the absolute maximum $U=1$ at the principal angle.

In practice, one can preferably work at $\theta=\pi/4$ or at the absolute maximum $U=1$, in which case the two formulas for y are identical. Otherwise, if an estimate of the principal angle is not available, then the y values can be calculated both ways, and then the correct value determined by evaluating $$-\beta_{calc} = \tan^{-1}\left(\frac{2y}{x^2+y^2+1}\right) \text{ and}$$

$$U_{calc} = \frac{y\sin^2(2\theta)}{[1+\cos^2(2\theta)][\cos(\beta_{calc})+y\sin(\beta_{calc})]-2x\cos(\beta_{calc})\cos(2\theta)},$$

and comprising values with the the known experimental values of $\beta$ and U. To determine $\epsilon$ experimentally, one measures the reflected intensity to determine U and $\beta$ ($I_{ave}$ cancels out in the equations).

To determine the dielectric constant directly from the measured intensity data, equations (1.3) and (1.4) are substituted into F=x+iy, to yield F=F(U,$\beta$). Upon substitution into equation (1.2) an exact result is provided for $\epsilon=\epsilon(U,\beta)$. This is a novel ellipsometry analysis technique, providing significant practical advantages. It is not dependent upon numerical approximation formulations or frequency scans as are prior ellipsometry techniques, may utilize digitized intensity data at a single frequency, and may take advantage of lasers that generate elliptically-polarized radiation.

3. Utilizing the Ellipsometry Technique

Figure 5:
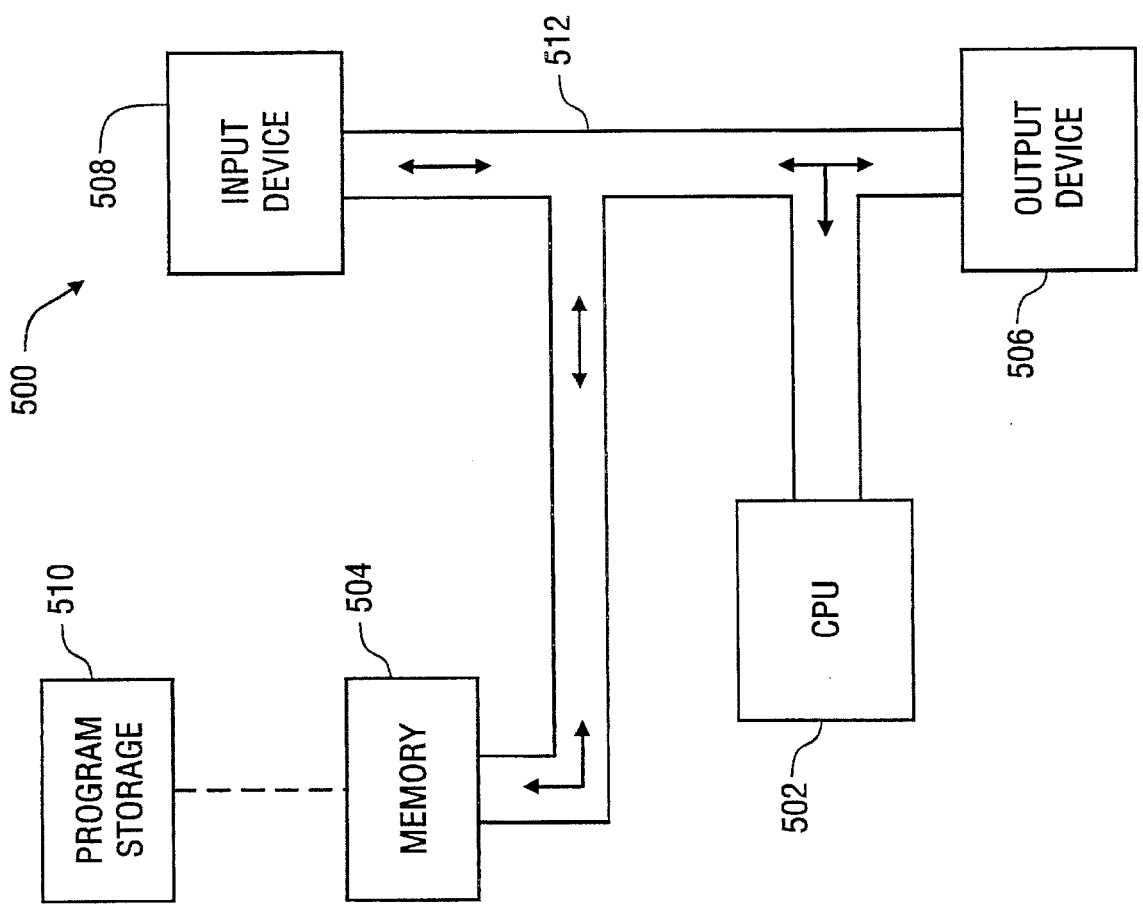
FIG. 5 is a computer system for analyzing optical data according to the present invention.

FIG. 5 shows a computer system 500 that may be used as data analyzer 110 according to the present invention for determining optical and spectroscopic properties of the sample material. One embodiment of an ellipsometry analysis technique 600 according to the present invention is described in the flow chart shown in FIG. 6. Computer system 500 includes a central processing unit 502, an input device 508, a program storage medium 510, a memory device 504, an output device 506, and a data/address bus 512. Central processing unit 502 is connected to memory 504, to input device 508, and to output device 506 through data/address bus 512. Ellipsometry analysis technique 600 includes four procedural blocks: 602, 604, 606 and 608.

Computer system 500 first loads ellipsometry analysis technique 600 into memory 504 from program storage medium 510. The program analytical listing, which is included at the end of this specification prior to the claims, implements this method, producing the complex index of refraction and the dielectric constant for the sample material. The data analysis program is written using the MATHCAD 5.0 program and was developed on a personal computer. This software is available from MathSoft, Inc., 101 Main Street, Cambridge, Mass. 02142.

Program storage medium 510 may be any machine readable storage medium such as a floppy or hard magnetic disk, an optical disk, or a programmable read-only memory. Computer system 500 may be a IBM personal computer. However, it will be understood that the particular hardware can be of other types. Acceptable alternatives include computer systems manufactured by, for example, Digital Equipment Corporation, International Business Machines, Sun Microsystems, or Hewlett-Packard. Versions of the program for other computer systems are readily producible by practitioners skilled in the art.

Figure 6:
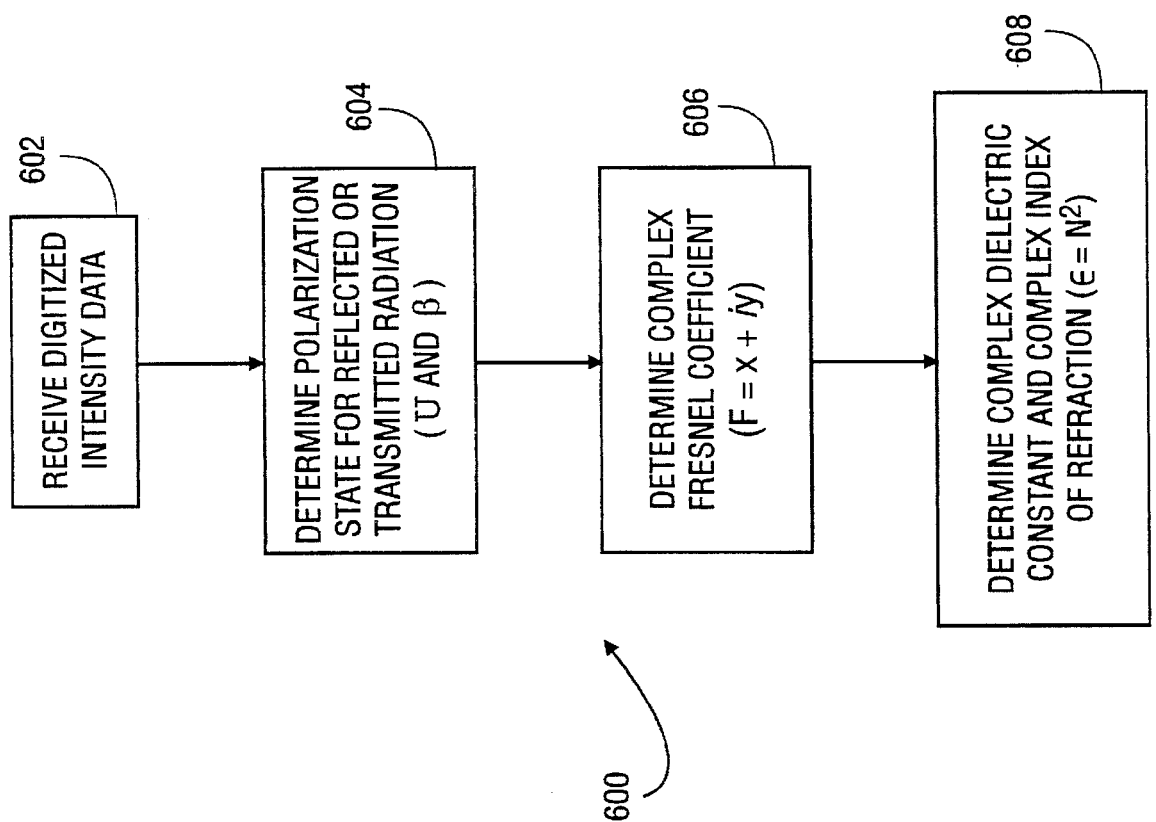
FIG. 6 a flow chart of the optical data analysis according to the present invention.

Once the determination method 600 of the present invention is loaded into memory 504, it is processed by central processing unit 502, which provides data analyzer 110. FIG. 6 is a flow chart for an embodiment of an ellipsometry technique for analyzing the digitized radiation intensity data according to the present invention. In process step 602, the data analyzer 110 receives the digitized intensity data 126 and/or 128 and angular position data 326 from the detection system 108. In process step 604, the data analyzer 110 determines the polarization state for the reflected or transmitted radiation from the received digitized intensity data. The polarization state is defined by U and $\beta$ as discussed below, and can be checked by corresponding experimental measurements for U and $\beta$. In process step 606, data analyzer 110 determines the complex Fresnel coefficient. This determination is conducted using the equation F=x+iy, using the determined polarization state. In process step 608, data analyzer 110 determines the complex dielectric constant $\epsilon$ and the complex index of refraction utilizing the determined Fresnel coefficient and the angle of incidence ($\epsilon=N^2=(n+ik)^2$).

As further explanation, the intensity data from the detector system with no sample material in place is given the designation $U_o$. This measurement represents the incident radiation. The intensity data from the detector system with a sample material in place is given the designation $U_i$ (for each known angular position i of the analyzer with respect to the known fixed axis). This measurement represents the reflected or transmitted radiation after it strikes the sample material. A equation-numerical calculation-plot example is presented below.

EXAMPLE

STEP 1: First, simulated data for the normalized input intensities $U_{o_i}$ and the normalized reflected intensities $U_i$ is input to provide an illustrative example. Thus, the digital analysis begins by converting digitized intensity data into $U_i$ versus i plots that are represented by the equation $I=I_{ave}(1+U\sin(2\psi+\beta))$.

The average intensities for both the incident radiation and the reflected radiation in arbitrary units are then calculated as follows:

$I_0$=mean ($v_0$)=avg. intensity incident=6.7

$I_1$=mean ($v_1$)=avg. intensity reflected=1.07

The quantities $U_o$ and $U_i$ for both incident radiation beam and reflected radiation beam ratios are then formed as follows:

$$U_{0_i} = \frac{v_{0_i}}{I_0} - 1 \quad U_i = \frac{v_i}{I_1} - 1$$

STEP 2: The digital analysis then determines U and $\beta$ for each beam from the following Fourier analysis of these signals:

incident beam $$x_0 = \sum_{i=0}^{NumSteps-1} U_{0_i} \sin(2 \cdot \Delta \cdot i)$$

and

-continued $$y_0 = \sum_{i=0}^{NumSteps-1} U_{0_i} \cos(2 \cdot \Delta \cdot i)$$

$x_0 = 0.7$ and $y_0 = -6.362$ $\beta_0 = \arctan(x_0, y_0) = 0.2$ $$U_0 = \sqrt{x_0^2 + y_0^2} \cdot \left( \frac{2}{NumSteps} \right) = 0.2$$

$$F_y(U,\beta,\eta,\theta) := U \cdot \cos(\beta) \cdot \frac{1 + \cos(2 \cdot \theta)^2 - U \cdot \sin(\beta) \cdot \sin(2 \cdot \theta)^2 + 2 \cdot \cos(2 \cdot \theta) \cdot \eta \cdot \sqrt{(1+U)(1-U)}}{\sin(2 \cdot \theta)^2 - 2 \cdot U \cdot \sin(\beta) \cdot (1 + \cos(2 \cdot \theta)^2) + U^2 \cdot \left[ \left( \frac{1 + \cos(2 \cdot \theta)^2}{\sin(2 \cdot \theta)} \right)^2 - \cos(\beta)^2 \cdot \sin(2 \cdot \theta)^2 \right]}$$

= imaginary part of Fresnel coefficient $F$ for $\sigma$ component

-continued reflected radiation beam

Establish:

$$x := \sum_{i=0}^{NumSteps-1} U_i \cdot \sin(2 \cdot \Delta \cdot i)$$

$$y := \sum_{i=0}^{NumSteps-1} U_i \cdot \cos(2 \cdot \Delta \cdot i)$$

$x = -0.842$ and $y = -6.041$ $\beta_1 = \arctan(x, y) = 4.574$

STEP 3: Using the equations above to obtain f from U and $\beta$ for each beam:

$$U_1 = \sqrt{x^2 + y^2} \cdot \left( \frac{2}{Numsteps} \right) = 0.191$$

$fy = F_y(U_1, \beta_1, \eta, \theta)$  $fy = -0.058$  $f_{y0} = y(U_0, \beta_0, \eta, \theta)$
$fx = F_x(fy, \beta_1)$  $fx = -0.408$  $f_{x0} = F_x(f_{y0}, \beta_0)$
$f = f_x + i \cdot f_y$  $f_0 = f_{x0} + i \cdot f_{y0}$ STEP 4: Obtaining G from f and $\theta$ for each beam:

$g = G(f, \theta)$  $g_0 = G(f_0, \theta)$

STEP 5: Obtaining the complex Fresnel coefficient F:

$$F = r\left( \frac{f_0}{g_0}, \frac{f}{g}, \theta \right) \quad F = -0.934 - 0.204i$$

STEP 6: Finally, obtaining $\epsilon$ and N:

$\epsilon = \epsilon(F, \theta)$  $\epsilon = -61.11 + 27.2i$ $N = \sqrt{\epsilon}$  $N = 1.7 + 8i$ Further modifications and alternative embodiments of this invention will be apparent to those skilled in the art in view of this description. Accordingly, this description is to be construed as illustrative only and is for the purpose of teaching those skilled in the art the manner of carrying out the invention. It is to be understood that the forms of the invention herein shown and described are to be taken as the presently preferred embodiments. Various changes may be made in the shape, size, and arrangement of parts. For example, equivalent elements or materials may be substituted for those illustrated and described herein, and certain features of the invention may be utilized independently of the use of other features, all as would be apparent to one skilled in the art after having the benefit of this description of the invention.

The following analytical listings implement ellipsometry analysis method 600, and are utilized by the computer programs described above.

Let $\theta$=angle of incidence and where $\eta=+1$ for $0<\theta<$Principle Angle; $\eta=-1$ for Principle Angle $<\theta<\pi/2$ Let $F_x(y,\beta) := -\sqrt{1 + 2 \cdot y \cdot \tan(\beta) - y^2}$ =real part of Fresnel coefficient F for $\sigma$ component:

Let $$G(F,\theta) := F \cdot \left( \frac{\cos(2 \cdot \theta) - F}{1 - F \cdot \cos(2 \cdot \theta)} \right) =$$

Fresnel coefficient $G$ for $\pi$ component

Let NumSteps=number of measurements made per $2\pi$ rotation in simulation

Let $i := 0..NumSteps-1$ index the individual measurements

Let $$\Delta := \frac{2 \cdot \pi}{Numsteps} =$$

angle of rotation between successive measurements and $\theta_i := \Delta \cdot i$ =angles at which measurements are made STEP 1: measure the intensity of incident beam; arbitrary units v0=voltage measured by the detector due to incident beam out of the laser:

STEP 2: measure the intensity of reflected beam (beam reflected off the sample); arbitrary units v=voltages measured by the detector due to beam reflected from sample:

STEP 3: calculate the average intensity for both beams; arbitrary units $I_0 :=$ mean($v_0$)=ave 'intensity0'  $I_1 :=$ mean($v$)=ave 'intensity'

STEP 4: calculate the deviations for both beams $$U_{0_i} := \frac{v_{0_i}}{I_0} = U_{SIMUL\_incident} \sin(2\psi + \beta_{SIMUL\_incident})$$

$$U_i := \frac{v_i}{I_1} = U_{SIMUL\_refl} \sin(2\psi + \beta_{SIMUL\_refl})$$

STEP 5: Fourier analyze these signals to obtain U and $\beta$ for each beam incident beam $$x_0 := \sum_{i=0}^{NumSteps-1} U_{0_i} \cdot \sin(2 \cdot \Delta \cdot i)$$

$$y_0 := \sum_{i=0}^{NumSteps-1} U_{0_i} \cdot \cos(2 \cdot \Delta \cdot i)$$

$$\beta_0 := \text{angle}(x_0, y_0) \quad U_0 := \sqrt{x_0^2 + y_0^2} \cdot \frac{2}{NumSteps}$$

reflected beam $$x := \sum_{i=0}^{NumSteps-1} U_i \cdot \sin(2 \cdot \Delta \cdot i)$$

$$y := \sum_{i=0}^{NumSteps-1} U_i \cdot \cos(2 \cdot \Delta \cdot i)$$

$$\beta_1 := \text{angle}(x, y) \quad U_1 := \sqrt{x^2 + y^2} \cdot \frac{2}{NumSteps}$$

STEP 6: to obtain F*a from U and β for each beam
$f_y := F_y(U_P, \beta_1, \eta, \theta) \quad f_{y0} := F_y(U_0, \beta_0, \eta, \theta)$
$f_x := F_x(f_y, \beta_1) \quad f_{x0} := F_x(f_{y0}, \beta_0)$
$f := f_x + i \cdot f_y \quad f_0 := f_{x0} + i \cdot f_{y0}$ STEP 7: Obtain G*b from f and θ for each beam $g := G(f, \theta)$
$g_0 := G(f_0, \theta)$ STEP 6: Obtain F Let $r(\xi_0, \xi, \theta) := \dfrac{\xi_0 \cdot \cos(2 \cdot \theta) - \xi}{\xi_0 - \xi \cdot \cos(2 \cdot \theta)}$ Fresnel coefficient F for σ component in terms of $\xi = f/g$ for incident and reflected waves then $F := r\left(\dfrac{f_0}{g_0}, \dfrac{f}{1g}, \theta\right)$ STEP 9: Obtain ε and N Let $\epsilon(F, \theta) := \dfrac{1 - 2 \cdot F \cdot \cos(2 \cdot \theta) + F^2}{(1+F)^2}$ dielectric constant as a function of Fresnel coefficient F for σ component and angle of incidence then $\epsilon := \epsilon(F, \theta)$ $N := \sqrt{\epsilon}$ The imaginary part of the Fresnel coefficient, F, for perpendicularly polarized radiation, σ, $$F_y(U, \beta, \eta, \theta) := U \cdot \cos(\beta) \cdot \frac{1 + \cos(2 \cdot \theta)^2 - U \cdot \sin(\beta) \cdot \sin(2 \cdot \theta)^2 + 2 \cdot \cos(2-\theta) \cdot \eta \cdot \sqrt{(1+U) \cdot (1-U)}}{\sin(2 \cdot \theta)^2 - 2 \cdot U \cdot \sin(\beta) \cdot (1 + \cos(2 \cdot \theta)^2) + U^2 \cdot \left[\left(\dfrac{1 + \cos(2 \cdot \theta)^2}{\sin(2 \cdot \theta)}\right)^2 - \cos(\beta)^2 \cdot \sin(2 \cdot \theta)^2\right]}$$

Note that η=+1 for 0<θ<Principle Angle; η=−1 for Principle Angle <θ<π2.

The real part of Fresnel coefficient, F, for σ component:

$F_x(y, \beta) := -\sqrt{1 + 2 \cdot y \cdot \tan(\beta) - y^2}$

Starting with Snell's Law, reflectivities, and intermediate equations we found the sample dielectric function in terms of F and the angle of incidence, θ, as seen below.

$\theta_r(\theta, m) := a\sin\left(\dfrac{\sin(\theta)}{m}\right)$
Snell's Law; m = relative index of refraction $r_a(\theta, m) := \dfrac{\cos(\theta) - m \cdot \cos(\theta_r(\theta, m))}{\cos(\theta) + m \cdot \cos(\theta_r(\theta, m))}$
Fresnel coefficient, F, (σ reflectivity)

The observed light intensity, I, is given by
$I := (|a \cdot \cos(\psi) + b \cdot \sin(\psi)|)_0^2$ We mathematically deifne:
$(|a \cdot \cos(\psi) + b \cdot \sin(\psi)|)^2 := I_{ave} \cdot (1 + U \cdot \sin(2 \cdot \psi + \beta)_0$ We introduced the ratio $b/2 = \xi$ from U and β:

$\xi(U, \beta, \eta) := \dfrac{U \cdot \cos(\beta) + i \cdot \eta \cdot \sqrt{(1+U) \cdot (1-U)}}{1 + U \cdot \sin(\beta)}$ $r(\xi_0, \xi, \theta) := \dfrac{\xi_0 \cdot \cos(2 - \theta) - \xi}{\xi_0 - \xi \cdot \cos(2 \cdot \theta)}$
Fresnel coefficient F for σ component in terms of the ratio of radiation intensities, $\dfrac{b}{a}$, (as seen below) for incident and reflected waves $G(F, \theta) := F \cdot \left(\dfrac{\cos(2 \cdot \theta) - F}{1 - F \cdot \cos(2 \cdot \theta)}\right)$
Fresnel coefficient, G, (π reflectivity)

$\Xi(\theta, m) := \dfrac{-r_a(\theta, m) + \cos(2 \cdot \theta)}{1 - r_a(\theta, m) \cdot \cos(2 \cdot \theta)}$
This is the ratio G/F from the Fresnel coefficient for the σ polarized radiation component $\xi(F, \theta) := \dfrac{1 - 2 \cdot F \cdot \cos(2 \cdot \theta) + F^2}{(1 + F)^2}$
The dielectric constant as a function of the Fresnel coefficient F for the σ component of polarization and the angle of inicidence.

Preparing to simulate the experimental data, we have found a function Z(ξ) with the simple connection to U as seen below.

$Z(\xi) := \dfrac{1}{1 + (|\xi|)^2} \cdot [2 \cdot Re(\xi) + i \cdot [1 - (|\xi|)^2]]$ where; $U(\xi) := |Z(\xi)|$ and $\beta(\xi) := \text{angle}(Re(Z(\xi)), Im(Z(\xi)))$ Assume a model index of refraction: $N_{MODEL} \equiv 1.7 + i \cdot 8$
As is well known the model dielectric constant is related to the index of refraction as:

$\epsilon_{MODEL} \equiv N_{MODEL}^2$

In our model take the plus sign of η: η≡1

We then in a simulation, calculated the model Fresnel coefficient F using the model dielectric constant:

$F_{SIMUL\_refl} := r_a(\theta, N_{MODEL}) \quad F_{SIMUL\_refl} = -0.934 - 0.204i$ The simulation checks with the assumed numerical optical values given above:

$\epsilon(F_{SIMUL\_refl}, \Theta) = -61.11 + 27.2i \quad \epsilon_{MODEL} = -61.11 + 27.2i$ -continued $$\sqrt{\epsilon(F_{SIMUL\_refl},\Theta)} = 1.7 + 8i \quad N_{MODEL} = 1.7 + 8i$$

We simulate incident intensities, U and β values (from the laser) beam:

$I_{SIMUL\_incident} := 6.7 \quad U_{SIMUL\_incident} := 0.2 \quad \beta_{SIMUL\_incident} := 4.822$ We also let:

$$\Theta := \frac{\pi}{4} \cdot 0.567 = \text{angle of incidence}$$

Remembering ξ=b/a for the beam incident on the sample:

$\xi_{SIMUL\_incident} := \xi(U_{SIMUL\_incident}, \beta_{SIMUL\_incident}, \eta) \quad \xi_{SIMUL\_incident} = 0.027 + 1.223i$ The ratio b/a for the beam reflected off of the sample is:
$\xi_{SIMUL}\text{refl} := (\Theta, N_{MODEL}) \cdot \xi_{,SIMUL\_incident}$
Recalling: $\xi_{SIMUL\_refl} = -0.032 + 1.21i$
Defining: $F_{TEST} := r(\xi_{SIMUL\_incident}, \xi_{SIMUL\_refl}, \Theta)$
Checking: $F_{TEST} = -0.934 - 0.204i$ and $F_{SIMUL}\text{refl} := -0.934 - 0.204i$
Simulate reflected intensities (off the sample) beam:

$I_{SIMUL\_refl} := 6.07 \quad U_{SIMUL\_refl} := U(\xi_{SIMUL\_refl}) \quad \beta_{SIMUL\_refl} := \beta(\xi_{SIMUL\_refl})$ Simulate voltages measured by the detector:
NumSteps:=64=number of measurements made per $2\pi$ rotation in simulation
i:=0..NumSteps−1

$$\Delta := \frac{2 \cdot \pi}{\text{NumSteps}}$$

$\theta_i := \Delta \cdot i$ the simulated voltages measured by the detector due to the beam reflected from the sample:

$v_i := I_{SIMUL\_refl}(1 + U_{SIMUL\_refl} \sin(2\theta_i + \beta_{SIMUL\_refl}))$ Also simulate voltages measured by the detector due to the radiation beam from the laser source:

$v_{0_i} := I_{SIMUL\_incident}(1 + U_{SIMUL\_incident} \sin(2\theta_i + \beta_{SIMUL\_incident}))$

STEP 1: Calculate the average intensity for both beams; arbitrary units $I_0 := \text{mean}(v_0) = \text{ave 'intrensity'} = I_0 = 6.7 \quad \text{check: } I_{SIMUL\_incident} := 6.7$ $I_i := \text{mean}(v) = \text{ave 'intrensity'} = I_1 = 6.07 \quad \text{check: } I_{SIMUL\_refl} := 6.07$

STEP 2: Form the quantities below for both incident and reflected radiation beam ratios.

$$U_{0_i} := \frac{v_{0_i}}{I_0} - 1 = U_{SIMUL\_incident} \sin(2\psi + \beta_{SIMUL\_incident})$$

$$U_i := \frac{v_i}{I_1} - 1 = U_{SIMUL\_refl} \sin(2\psi + \beta_{SIMUL\_refl})$$

STEP 3: Fourier analyze these signals to obtain U and β for each beam

Reflected beam

Establish:

$$x := \sum_{i=0}^{\text{NumSteps}-1} U_i \cdot \sin(2 \cdot \Delta \cdot i)$$

$$y := \sum_{i=0}^{\text{NumSteps}-1} U_i \cdot \cos(2 \cdot \Delta \cdot i)$$

Calculating: $x = -0.842$ and $y = -6.041$

We have:
$\beta_1 := \text{angle}(x,y) \quad \beta_1 = 4.574$ and checking: $\beta_{SIMUL\_refl} = 4.574$
$U_1 := \sqrt{x^2 + y^2} \cdot \frac{2}{\text{NumSteps}} \quad U_1 = 0.191$ and
check: $U_{SIMUL\_refl} = 0.191$ Incident beam $$x_0 := \sum_{i=0}^{\text{NumSteps}-1} U_{0_i} \cdot \sin(2 \cdot \Delta \cdot i) \text{ and}$$

$$y_0 := \sum_{i=0}^{\text{NumSteps}-1} U_{0_i} \cdot \cos(2 \cdot \Delta \cdot i)$$

Results in: $x_0 = 0.7$ and $y_0 = -6.362$ $\beta_0 := \text{angle}(x_0, y_0) \quad \beta_0 = 4.822$ checking: $\beta_{SIMUL\_incident} = 4.822$ $$U_0 := \sqrt{x_0^2 + y_0^2} \cdot \frac{1}{\text{NumSteps}} \quad U_0 = 0.2$$

checking: $U_{SIMUL\_incident} = 0.2$

STEP 4: to obtain F*a from U and β for each beam $f_y := F_y(U_1, \beta_1, \eta, \Theta) \quad f_y = -0.058 \quad f_{y0} := F_y(U_0, \beta_0, \eta, \Theta)$
$f_x := F_x(f_y, \beta_1) \quad f_x = -0.408 \quad f_{x0} := F_x(f_{y0}, \beta_0)$
$f := f_x + i \cdot f_y \quad f_0 := f_{x0} + i \cdot f_{y0}$

STEP 5: Obtain G*b from f and θ for each beam
$g := G(f, \theta) \quad g_0 := G(f_0, \theta)$
STEP 6: Obtain F $$F_{SIMUL} := r\left(\frac{f_0}{g_0}, \frac{f}{g}, \Theta\right)$$

$F_{SIMUL} = -0.934 - 0.204i$ checking: $F_{SIMUL\_refl} = -0.934 - 0.204i$
STEP 7: Obtain ε and N
$\epsilon_{SIMUL} := \epsilon(F_{SIMUL}, \theta) \quad \epsilon_{SIMUL} = -61.11 + 272i$
Checking: $\epsilon_{MODEL} = -61.11 + 27.2i$
Likewise:
$N_{SIMUL} := \sqrt{\epsilon_{SIMUL}} \quad N_{SIMUL} = 1.7 + 8i$
Checking: $N_{MODEL} = 1.7 + 8i$
Intensity:

$I = |a\cos(\psi) + b\sin(\psi)|^2 = [a\cos(\psi) + b\sin(\psi)][\bar{a}\cos(\psi) + \bar{b}\sin(\psi)]$ $= |a|^2\cos^2(\psi) + |b|^2\sin^2(\psi) + (a\bar{b} + \bar{a}b)\sin(\psi)\cos(\psi)$ $= |a|^2\frac{1+\cos(2\psi)}{2} + |b|^2\frac{1-\cos(2\psi)}{2} + \frac{1}{2}\sin(2\psi)(a\bar{b} + \bar{a}b)$ $= \frac{1}{2}(|a|^2 + |b|^2) + \frac{1}{2}(|a|^2 - |b|^2)\cos(2\psi) + \frac{1}{2}\sin(2\psi)(a\bar{b} - \bar{a}b)$ $= \frac{1}{2}(|a|^2 + |b|^2)\left\{1 + \sin(2\psi)\frac{a\bar{b} + \bar{a}b}{|a|^2 + |b|^2} + \cos(2\psi)\frac{|a|^2 - |b|^2}{|a|^2 + |b|^2}\right\}$ $= \frac{1}{2}(|a|^2 + |b|^2)\left\{1 + \sin(2\psi)\frac{\xi + \bar{\xi}}{1 + |\xi|^2} + \cos(2\psi)\frac{1 - |\xi|^2}{1 + |\xi|^2}\right\},$ -continued where $\xi = \frac{b}{a}$ $= \frac{1}{2} (|a|^2 + |b|^2)\{1 + \sin(2\psi)U\cos(\beta) + \cos(2\psi)U\sin(\beta)\}$ $= \frac{1}{2} (|a|^2 + |b|^2)\{1 + U\sin(2\psi + \beta)\} \equiv I_{ave}\{1 + U\sin(2\psi + \beta)\},$ where $U\cos(\beta) = \frac{\xi + \bar{\xi}}{1 + |\xi|^2}$  $U\sin(\beta) = \frac{1 - |\xi|^2}{1 + |\xi|^2}$ Note that $1 + U\sin(\beta) = \frac{2}{1 + \xi\bar{\xi}} \Rightarrow \xi\bar{\xi} = \frac{1 - U\sin(\beta)}{1 + U\sin(\beta)} \Rightarrow \bar{\xi} = \frac{1}{\xi} \frac{1 - U\sin(\beta)}{1 + U\sin(\beta)}$ and -continued $2U\cos(\beta) = \frac{2}{1 + |\xi|^2} (\xi + \bar{\xi}) =$ $(1 + U\sin(\beta))(\xi + \bar{\xi}) = \xi(1 + U\sin(\beta)) + \frac{1}{\xi}(1 - U\sin(\beta))$ $\left\langle \beta \to -\beta \Rightarrow \xi \to \frac{1}{\xi} \right\rangle$ $\Rightarrow \xi = \frac{U\cos(\beta) \pm i\sqrt{1 - U^2}}{1 + U\sin(\beta)}$ Fresnel Coefficients $\tilde{r}_\perp = \frac{\cos(\theta_i) - m\cos(\theta_t)}{\cos(\theta_i) + m\cos(\theta_t)} \Rightarrow m\cos(\theta_t) = \cos(\theta_i) \frac{1 - \tilde{r}_\perp}{1 + \tilde{r}_\perp}$ $m^2\cos^2(\theta_t) = m^2 - m^2\sin^2(\theta_t) = m^2 - \sin^2(\theta_i) = \cos^2(\theta_i) \left( \frac{1 - \tilde{r}_\perp}{1 + \tilde{r}_\perp} \right)^2$ $\Rightarrow \epsilon \equiv m^2 = \frac{\sin^2(\theta_i)(1 + \tilde{r}_\perp)^2 + \cos^2(\theta_i)(1 - \tilde{r}_\perp)^2}{(1 + \tilde{r}_\perp)^2} = \frac{1 + \tilde{r}_\perp^2 - 2\tilde{r}_\perp\cos(2\theta_i)}{(1 + \tilde{r}_\perp)^2}$ $= \frac{1 + 2\tilde{r}_\perp + \tilde{r}_\perp^2 - 2\tilde{r}_\perp - 2\tilde{r}_\perp\cos(2\theta_i)}{(1 + \tilde{r}_\perp)^2}$ $= \frac{(1 + \tilde{r}_\perp)^2 - 4\tilde{r}_\perp\cos^2(\theta_i)}{(1 + \tilde{r}_\perp)^2} = 1 - \frac{4\tilde{r}_\perp\cos^2(\theta_i)}{(1 + \tilde{r}_\perp)^2}$ $\tilde{r}_\parallel = \frac{\cos(\theta_t) - m\cos(\theta_i)}{\cos(\theta_t) + m\cos(\theta_i)} \Rightarrow m\cos(\theta_i) = \cos(\theta_t) \frac{1 - \tilde{r}_\parallel}{1 + \tilde{r}_\parallel}$ $\frac{\cos(\theta_i)}{\cos(\theta_t)} = \frac{1}{m} \frac{1 - \tilde{r}_\parallel}{1 + \tilde{r}_\parallel} = m \frac{1 + \tilde{r}_\perp}{1 - \tilde{r}_\perp}$ $\Rightarrow (1 - \tilde{r}_\parallel)(1 - \tilde{r}_\perp) = m^2(1 + \tilde{r}_\parallel)(1 + \tilde{r}_\perp) = \frac{1 + \tilde{r}_\perp^2 - 2\tilde{r}_\perp\cos(2\theta_i)}{(1 + \tilde{r}_\perp)^2} (1 + \tilde{r}_\parallel)(1 + \tilde{r}_\perp)$ $\Rightarrow (1 - \tilde{r}_\parallel)(1 - \tilde{r}_\perp)(1 + \tilde{r}_\perp) = (1 + \tilde{r}_\parallel)(1 + \tilde{r}_\perp^2 - 2\tilde{r}_\perp\cos(2\theta_i))$ $\Rightarrow \tilde{r}_\parallel = \tilde{r}_\perp \left( \frac{-\tilde{r}_\perp + \cos(2\theta_i)}{1 - \tilde{r}_\perp\cos(2\theta_i)} \right)$ If $\frac{b}{a} \equiv \xi = \lambda \frac{\tilde{r}_\parallel}{\tilde{r}_\perp} = \lambda \frac{-\tilde{r}_\perp + \cos(2\theta_i)}{1 - \tilde{r}_\perp\cos(2\theta_i)}$ $\Rightarrow \xi[1 - \tilde{r}_\perp\cos(2\theta_i)] = \lambda[-\tilde{r}_\perp + \cos(2\theta_i)]$ $\Rightarrow \tilde{r}_\perp = \frac{\lambda\cos(2\theta_i) - \xi}{\lambda - \xi\cos(2\theta_i)}$ If $\frac{b}{a} \equiv \xi = \frac{E_\parallel^{refl}}{E_\perp^{refl}} = \frac{E_\parallel^{inc}}{E_\perp^{inc}} \frac{\tilde{r}_\parallel}{\tilde{r}_\perp} = \frac{E_\parallel^{inc}}{E_\perp^{inc}} \left( \frac{-\tilde{r}_\perp + \cos(2\theta_i)}{1 - \tilde{r}_\perp\cos(2\theta_i)} \right)$ then $\vec{E}^{refl} = \hat{e}_\perp E_\perp^{refl} + \hat{e}_\parallel E_\parallel^{refl}$ $\hat{P} \cdot \vec{E}^{refl} = \hat{P} \cdot \hat{e}_\perp E_\perp^{refl} + \hat{P} \cdot \hat{e}_\parallel E_\parallel^{refl} \equiv a\cos(\psi) + b\sin(\psi)$ -continued $$\Rightarrow \xi[1 - \tilde{r}_\perp \cos(2\theta_i)] = \frac{E_\parallel^{inc}}{E_\perp^{inc}} [-\tilde{r}_\perp + \cos(2\theta_i)]$$

Let $\dfrac{E_\parallel^{inc}}{E_\perp^{inc}} \equiv \xi_0$ $$\Rightarrow \tilde{r}_\perp = \frac{\xi_0 \cos(2\theta_i) - \xi}{\xi_0 - \xi \cos(2\theta_i)},$$

where $\xi = \dfrac{U\cos(\beta) \pm i\sqrt{1-U^2}}{1 + U\sin(\beta)}$ $\quad \xi_0 = \dfrac{U_0\cos(\beta_0) \pm i\sqrt{1-U_0^2}}{1 + U_0\sin(\beta_0)}$ and $$\epsilon = \frac{1 + \tilde{r}_\perp^2 - 2\tilde{r}_\perp \cos(2\theta_i)}{(1 + \tilde{r}_\perp)^2}$$

What is claimed is:

1. An ellipsometry method for determining optical and spectroscopic properties of a material, comprising:
   subjecting a material to an incident radiation at a single frequency having a determined arbitrary elliptical polarization state;
   measuring at said single frequency a resultant radiation from said material due to interaction with said incident radiation;
   determining a polarization state for said resultant radiation said determining step, comprising:
   converting said resultant radiation into digitized intensity data representative of said resultant radiation;
   analyzing said digitized intensity data (I) to obtain values for U and β utilizing the equation:

$I = I_{ave}[1 + U \sin(2\Psi + \beta)]$, $I_{ave}$ representing an average intensity of said measured resultant radiation,
   Ψ representing a known angular difference between an angle of incidence of the incident radiation upon the sample material and a rotation angle of an analyzer measuring said resultant radiation,
   said values for U and β representing the polarization state of said resultant radiation through their proportionality to the polarization vectors of said resultant radiation; and
   utilizing said representation of the polarization state of said resultant radiation to determine an optical property of said material from modifications to said known polarization state of said incident radiation due to interaction with said material.

2. The ellipsometry method of claim 1, wherein said resultant radiation is radiation reflected by said material due to interaction with said incident radiation.

3. The ellipsometry method of claim 1, wherein said resultant radiation is radiation transmitted through said material due to interaction with said incident radiation.

4. The ellipsometry method of claim 1, wherein said material is a solid, homogenous material.

5. The ellipsometry method of claim 1, wherein said material is a fluid biological material.

6. The ellipsometry method of claim 1, wherein said optical property is a complex index of refraction for said material as a function of U and β.

7. The ellipsometry method of claim 1, wherein said optical property is a complex dielectric constant for said material as a function of U and β.

8. The method of claim 7, wherein said utilizing step comprises:
   determining an angle of incidence (θ) for said incident radiation;
   determining a principle angle (θ$^p$) for said material;
   calculating a value for the complex Fresnel coefficient (F) utilizing the equation F=x+iy, where $$y = \cos(\beta)U \frac{1 + \cos^2(2\theta) - \sin(\beta)\sin^2(2\theta)U + (\eta)2\cos(2\theta)\sqrt{1-U^2}}{\sin^2(2\theta) - 2U\sin(\beta)[1+\cos^2(2\theta)] + U^2\left[\dfrac{(1+\cos^2(2\theta))^2}{\sin^2(2\theta)} - \cos^2(\beta)\sin^2(2\theta)\right]} \quad (1.3)$$

said value for η being −1 for 0<θ<θ$^p$, and said value for η being +1 for θ$^p$<θ<π/2), and $$x = -\sqrt{1 + 2y\tan(\beta) - y^2} \; ; \quad (1.4)$$

and calculating a value for said dielectric constant (ε) utilizing the equation:

$$\epsilon = \frac{1 - 2F\cos(2\theta) + F^2}{(1+F)^2} \; . \quad (1.2)$$

9. An ellipsometry method for determining optical and spectroscopic properties of a material, comprising:
   subjecting a material to an incident radiation having a determined elliptical polarization state;
   measuring a resultant radiation from said material due to interaction with said incident radiation;
   creating digitized intensity data for said resultant radiation; and
   utilizing said digitized intensity data to determine a complex index of refraction or a complex dielectric constant for said material by:
   analyzing said digitized intensity data (I) to obtain values for U and β utilizing the equation:

$I = I_{ave}[1 + U \sin(2\Psi + \beta)]$, $I_{ave}$ representing an average intensity of said measured resultant radiation, Ψ representing a known angular difference between an angle of incidence of the incident radiation on the sample material and a rotation angle of an analyzer measuring said resultant radiation, said values for U and β representing the polarization state of said resultant radiation through their proportionality to the polarization vectors of said resultant radiation;

utilizing an angle of incidence (θ) for said incident radiation;

utilizing a principle angle (θ$^P$) for said material;

calculating a value for the complex Fresnel coefficient (F) utilizing the equation F=x+iy, where $$y = \cos(\beta)U \; \frac{1 + \cos^2(2\theta) - \sin(\beta)\sin^2(2\theta)U + (\eta)2\cos(2\theta)\sqrt{1-U^2}}{\sin^2(2\theta) - 2U\sin(\beta)[1+\cos^2(2\theta)] + U^2\left[\frac{(1+\cos^2(2\theta))^2}{\sin^2(2\theta)} - \cos^2(\beta)\sin^2(2\theta)\right]} \quad (1.3)$$

said value for η being −1 for 0<θ<θ$^P$, and said value for η being +1 for θ$^P$<θ<π/2), and $$x = -\sqrt{1 + 2y\tan(\beta) - y^2} \; ; \quad (1.4)$$

and calculating a value for said dielectric constant (ε) utilizing the equation:

$$\epsilon = \frac{1 - 2F\cos(2\theta) + F^2}{(1+F)^2} \quad (1.2)$$

10. The ellipsometry method of claim 9 wherein said incident radiation is at a single frequency.

11. An ellipsometer for determining optical and spectroscopic properties of a material, comprising:

a radiation source providing incident radiation of a definite polarization and frequency directed toward a material at a measurable angle of incidence;

a radiation detector positioned to receive resultant radiation after interaction of said incident radiation with said material; and a computer-controlled data analysis means for utilizing digitized intensity data for said resultant radiation to determine modifications to said polarization state of said incident radiation due to interaction with said material, said determining step comprising:

analyzing said digitized intensity data (I) to obtain values for U and β utilizing the equation:

I=I$_{ave}$[1+U sin(2Ψ+β)],

I$_{ave}$ representing an average intensity of said measured resultant radiation, Ψ representing a known angular difference between an angle of incidence of the incident radiation on the sample material and a rotation angle of an analyzer measuring said resultant radiation, said values for U and β representing the polarization state of said resultant radiation through their proportionality to the polarization vectors of said resultant radiation; and utilizing said representation of the polarization state of said resultant radiation to determine optical and spectroscopic properties of said material as a function of said modifications to said polarization state.

12. The rotating-analyzer ellipsometer of claim 11, wherein said radiation source comprises:

a solid state laser;

a linear polarizer in optical communication with said solid state laser; and a Fresnel Rhomb in optical communication with said linear polarizer.

13. The ellipsometer of claim 11, wherein said detector comprises:

a rotating linear polarizer (analyzer);

an integrating sphere in optical communication with said rotating linear polarizer; and a photodetector in optical communication with said integrating sphere.

14. The ellipsometer of claim 11, wherein said optical and spectroscopic properties are a complex index of refraction and a complex dielectric constant for said material.

15. The rotating-analyzer ellipsometer of claim 11, wherein said computer-controlled data analyzer means determine optical and spectroscopic properties by:

utilizing an angle of incidence (θ) for said incident radiation;

utilizing a principle angle (θ$^P$) for said material;

calculating a value for the complex Fresnel coefficient (F) utilizing the equation F=x+iy, where $$y = \cos(\beta)U \; \frac{1 + \cos^2(2\theta) - \sin(\beta)\sin^2(2\theta)U + (\eta)2\cos(2\theta)\sqrt{1-U^2}}{\sin^2(2\theta) - 2U\sin(\beta)[1+\cos^2(2\theta)] + U^2\left[\frac{(1+\cos^2(2\theta))^2}{\sin^2(2\theta)} - \cos^2(\beta)\sin^2(2\theta)\right]} \quad (1.3)$$

said value for η being −1 for 0<θ<θ$^P$, and said value for η being +1 for θ$^P$<θ<π/2), and $$x = -\sqrt{1 + 2y\tan(\beta) - y^2} \; ; \quad (1.4)$$

and calculating a value for said dielectric constant (ε) utilizing the equation:

$$\epsilon = \frac{1 - 2F\cos(2\theta) + F^2}{(1+F)^2} \; . \quad (1.2)$$

* * * * *

UNITED STATES PATENT AND TRADEMARK OFFICE
CERTIFICATE OF CORRECTION

PATENT NO.    :   5,625,455
DATED         :   April 29, 1997
INVENTOR(S)   :   Patrick L. Nash nd Robert J. Bell It is certified that error appears in the above-identified patent and that said Letters Patent is hereby corrected as shown below:

```
In claim 1, column 19, line 29, after "tion" insert --,--.
In claim 12, column 22, line 7, delete "rotating-analyzer".
```

Signed and Sealed this

Twenty-second Day of July, 1997

Attest:

BRUCE LEHMAN

*Attesting Officer*            *Commissioner of Patents and Trademarks*